United States Patent
Umebayashi

(10) Patent No.: US 8,845,503 B2
(45) Date of Patent: Sep. 30, 2014

(54) METHOD FOR MANUFACTURING DISPOSABLE WORN ARTICLE

(75) Inventor: Toyoshi Umebayashi, Osaka (JP)

(73) Assignee: Zuiko Corporation, Osaka (JP)

( * ) Notice: Subject to any disclaimer, the term of this patent is extended or adjusted under 35 U.S.C. 154(b) by 446 days.

(21) Appl. No.: 13/377,314

(22) PCT Filed: Jul. 13, 2010

(86) PCT No.: PCT/JP2010/061808
§ 371 (c)(1),
(2), (4) Date: Dec. 9, 2011

(87) PCT Pub. No.: WO2011/010574
PCT Pub. Date: Jan. 27, 2011

(65) Prior Publication Data
US 2012/0115700 A1    May 10, 2012

(30) Foreign Application Priority Data

Jul. 21, 2009   (JP) .................................. 2009-169948

(51) Int. Cl.
*B32B 37/12* (2006.01)
*B31B 1/14* (2006.01)
*A61F 13/15* (2006.01)

(52) U.S. Cl.
CPC ..... *A61F 13/15642* (2013.01); *A61F 13/15723* (2013.01)
USPC ............. 493/340; 493/331; 493/382; 156/66; 156/204; 156/227; 156/269

(58) Field of Classification Search
CPC .............. A61F 13/505; A61F 13/5611; A61F 13/5616; A61F 13/5622; A61F 13/5644; A61F 13/5655; A61F 13/15593; A61F 13/49009; A61F 13/49413; A61F 13/49466
USPC .................................. 156/250–253, 267, 269
See application file for complete search history.

(56) References Cited

U.S. PATENT DOCUMENTS 5,064,489 A    11/1991   Ujimoto et al.
(Continued)

FOREIGN PATENT DOCUMENTS

| JP | 1-162808 A | 6/1989 |
| JP | 2008-061693 A | 3/2008 |
| JP | 2008-155015 A | 7/2008 |

OTHER PUBLICATIONS

Shinnosuke, Morita, Production Method of Underpants-Type Wearing Article (Translation), Mar. 21, 2008, JP 2008-061693.*

(Continued)

*Primary Examiner* — Thanh Truong
*Assistant Examiner* — Chelsea Stinson
(74) *Attorney, Agent, or Firm* — Renner, Otto, Boisselle & Sklar, LLP

(57) ABSTRACT

A method comprising the steps of: carrying a continuous sheet W1 which is an external sheet 3 being continuous in the longitudinal direction X perpendicular to the girth direction Y; carrying a continuous laminate W2 which is an absorbent body 2 being continuous in the longitudinal direction X perpendicular to the girth direction Y; cutting off a tip portion of the continuous laminate W2 in the carrying direction X1 to obtain absorbent bodies 2 one after another; separating the cut-off absorbent bodies 2 from each other in the longitudinal direction X of the absorbent bodies; placing the absorbent bodies 2 in a detatchable manner and intermittently on the continuous sheet W1; and severing the continuous sheet W1 between the absorbent bodies 2, thereby obtaining individual worn articles 1 each having the absorbent body 2 placed on the external sheet 3.

5 Claims, 4 Drawing Sheets

(56) References Cited

U.S. PATENT DOCUMENTS

| | | | |
|---|---|---|---|
| 6,755,808 B2 * | 6/2004 | Balogh et al. | 604/385.28 |
| 8,440,039 B2 * | 5/2013 | Nakakado | 156/204 |
| 2009/0198207 A1 | 8/2009 | Torigoshi et al. | |

OTHER PUBLICATIONS

International Search Report for corresponding International Application No. PCT/JP2010/061808 mailed Oct. 19, 2010.

* cited by examiner

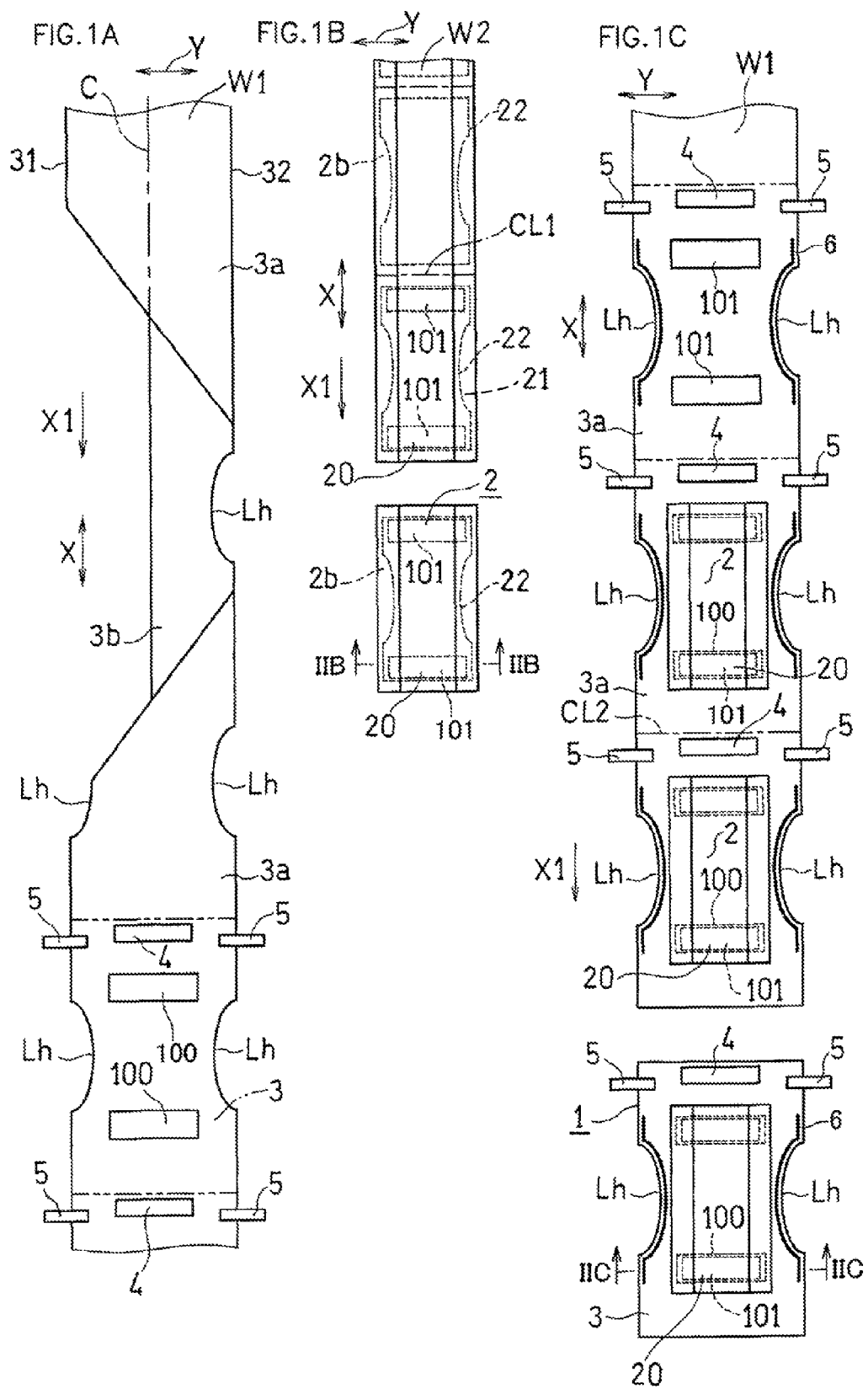

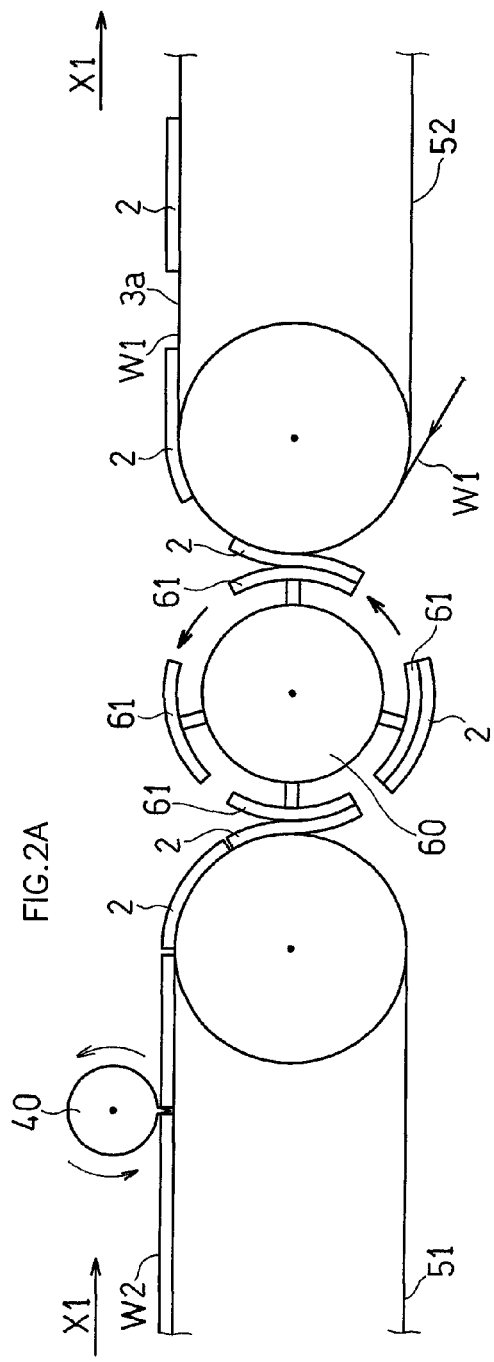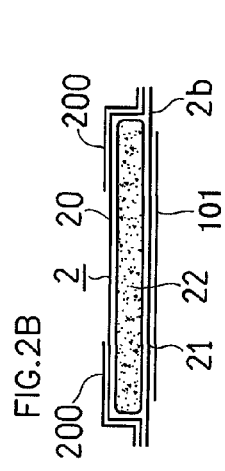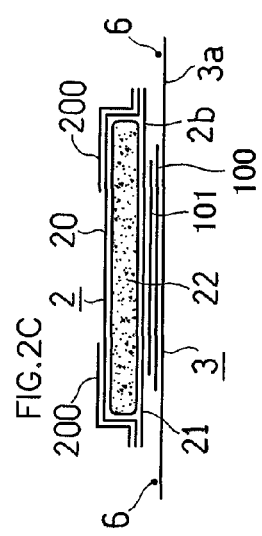

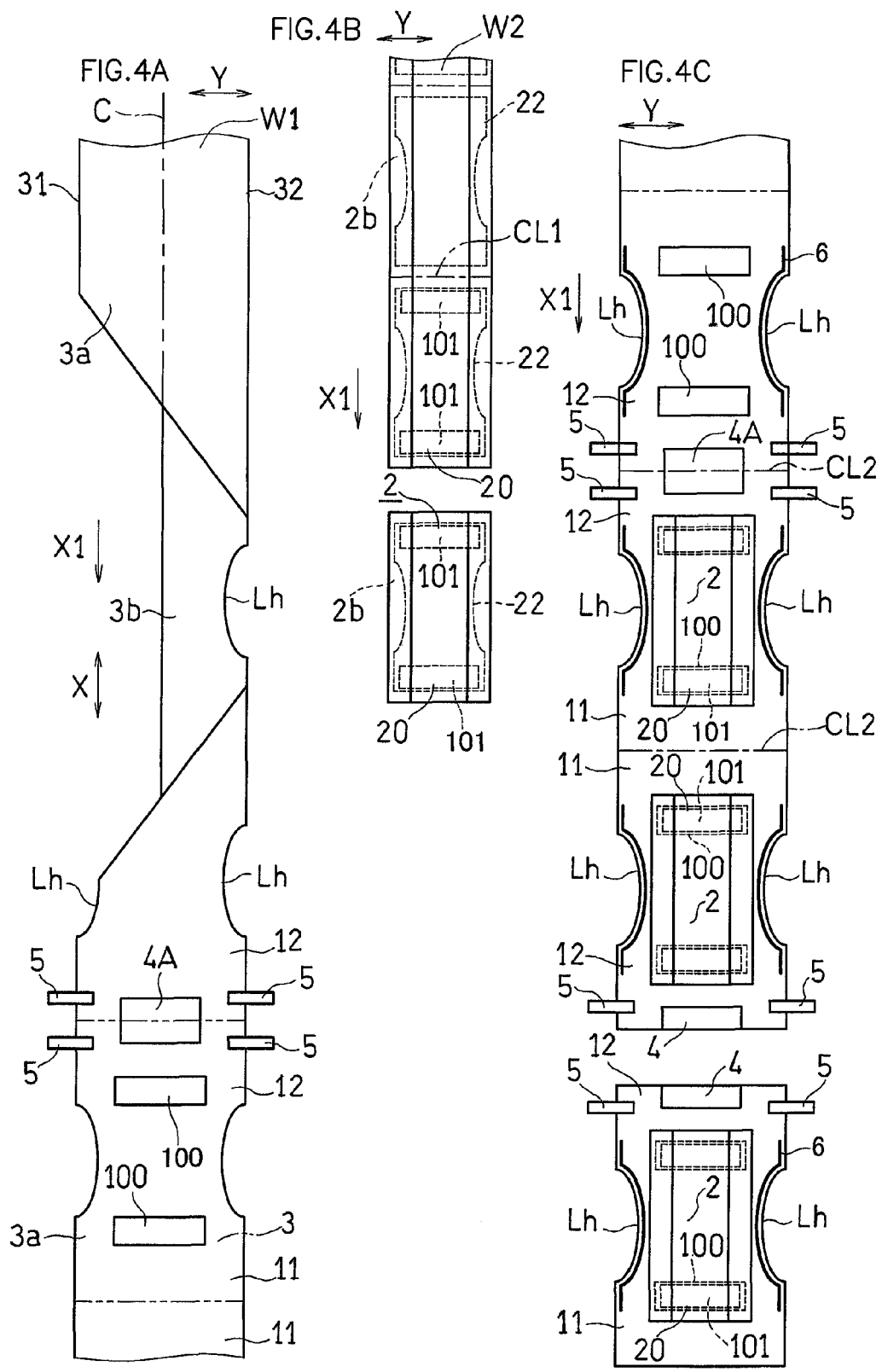

METHOD FOR MANUFACTURING DISPOSABLE WORN ARTICLE

TECHNICAL FIELD

The present invention relates to a method for manufacturing disposable worn articles.

BACKGROUND ART

Methods for manufacturing disposable worn articles while carrying sheets and cores in the longitudinal direction which is perpendicular to the girth direction have been proposed in the art (see the first patent document).

CITATION LIST

Patent Document

[FIRST PATENT DOCUMENT] Japanese Laid-Open Patent Publication No. 1-162808 (FIG. 4)

SUMMARY OF INVENTION

In the manufacturing method disclosed in the first patent document, liquid-absorbing cores are placed in an intermittent pattern between a continuous top sheet and a continuous back sheet to form a laminate, and then the laminate is cut and divided into individual disposable worn articles.

However, when a disposable worn article of the first patent document is worn, the waist portion on the front and back side of the wearer is covered by the liquid-impermeable back sheet, thereby causing dampness. Moreover, since the back sheet and the top sheet are present across the entire length of the disposable worn article, material becomes wasted.

It is therefore a primary object of the present invention to provide a method for manufacturing a disposable worn article that is less likely to cause dampness in the waist portion and that produces no waste of material.

A method for manufacturing a disposable worn article in one embodiment of the present invention is a method for manufacturing a disposable worn article (worn articles), the disposable worn article including: an absorbent body including a liquid-permeable top sheet, a liquid-impermeable back sheet and a liquid-absorbing core; and an air-permeable external sheet, wherein the external sheet covers a crotch portion of a wearer with the absorbent body interposed therebetween, and a waist portion thereof where the absorbent body is absent covers a waist of the wearer on a front side and on a back side, the method including the steps of: carrying a continuous sheet which is the external sheet being continuous in a longitudinal direction perpendicular to a girth direction; carrying a continuous laminate which is the absorbent body being continuous in the longitudinal direction; cutting off a tip portion of the continuous laminate in a carrying direction to obtain absorbent bodies one after another; separating the cut-off absorbent bodies from each other in the longitudinal direction of the absorbent bodies; placing the absorbent bodies in a detatchable manner and intermittently on the continuous sheet so that an inner surface of the external sheet is not covered by the absorbent body in the waist portion on the front side and on the back side; and severing the continuous sheet between adjacent absorbent bodies, thereby obtaining individual worn articles each having the absorbent body placed on the external sheet.

According to the present invention, the absorbent body is placed on the external sheet. Therefore, the absorbent body can be made shorter than the external sheet. The waist portion of the external sheet is not covered by the absorbent body. Thus, using a material having good air permeability (e.g., a non-woven fabric) as the external sheet improves the air permeability of the waist portion, thereby preventing dampness.

The top sheet and the back sheet form an absorbent body that is smaller than the external sheet. Therefore, the area of the top sheet and the back sheet is significantly reduced. Thus, there is no waste of material.

BRIEF DESCRIPTION OF THE DRAWINGS

FIGS. 1A to 1C are schematic plan views, each showing a method for manufacturing a disposable worn article according to Embodiment 1 of the present invention.

FIG. 2A is a schematic side view showing a part of the manufacturing step, FIG. 2B is a schematic cross-sectional view taken along line IIB-IIB of FIG. 1B, and FIG. 2C is a schematic cross-sectional view taken along line IIC-IIC of FIG. 1C.

FIGS. 4A to 4C are schematic plan views, each showing Embodiment 2.

MODE FOR CARRYING OUT THE INVENTION

Figure 3A:
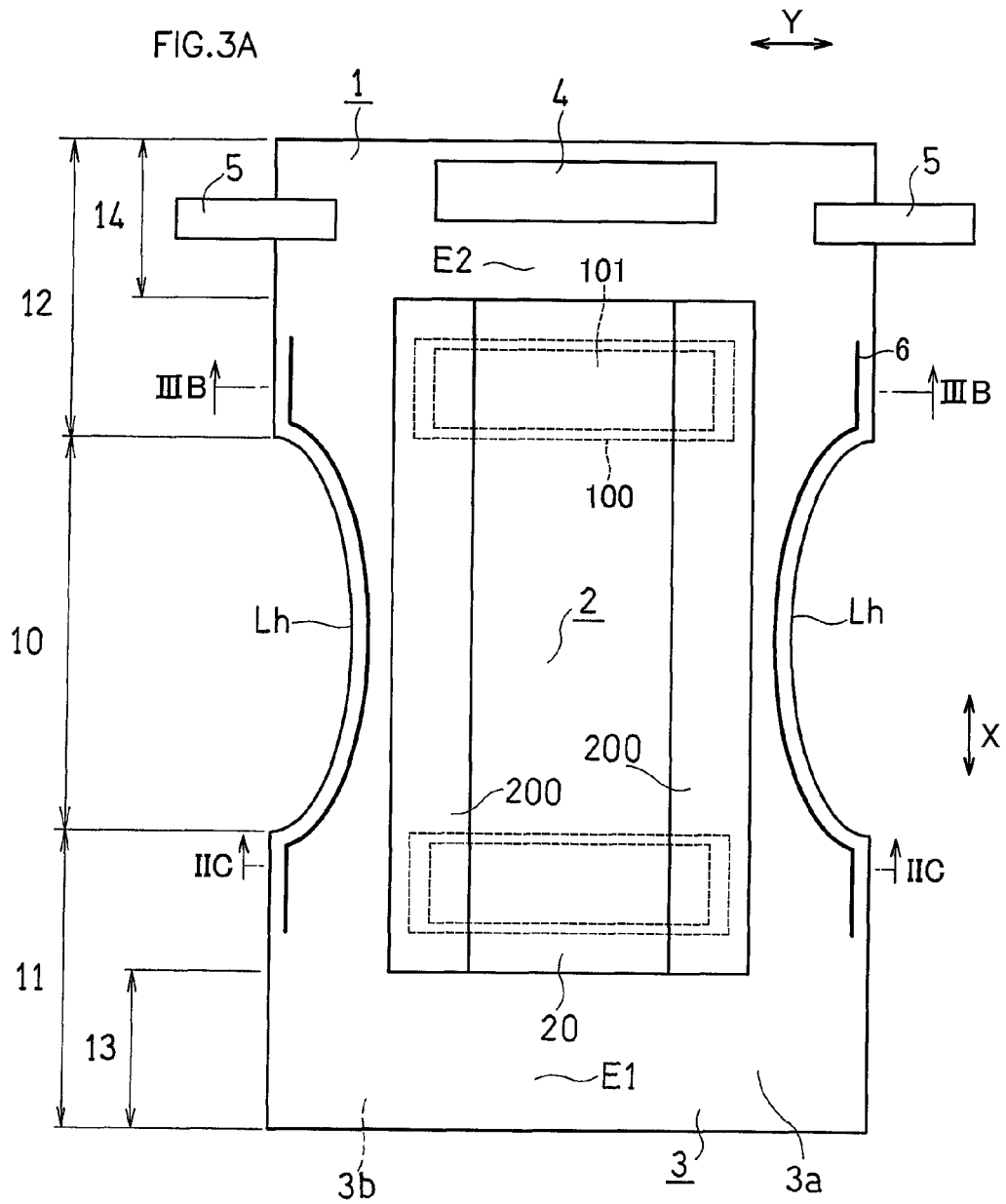
FIG. 3A is a schematic plan view showing a worn article manufactured by the manufacturing method.

In a preferred embodiment of the present invention, the external sheet includes an elastic band for expanding and contracting a rear waist portion thereof placed on the rear waist portion which covers the back side of the waist of the wearer, and the inner surface of the external sheet is exposed between the elastic band and the absorbent body so as to be in contact with skin of the wearer.

With such an embodiment, the elastic band provided on the rear waist portion makes the disposable worn article fit to the wearer around the waist, thus improving the wearability. Herein, the inner surface of the external sheet is exposed so as to be in contact with the skin between the elastic band and the absorbent body. Therefore, the air permeability is maintained in the rear waist portion.

In a preferred embodiment of the present invention, the method further includes the steps of; folding the continuous sheet in two so that a first side edge portion and a second side edge portion along the longitudinal direction of the continuous sheet lie on top of each other; and trimming a portion of the first and second side edge portions in a die-cutting process, with the first and second side edge portions lying on top of each other, so that a portion of the first and second side edge portions is narrowed.

With such an embodiment, after the continuous sheet is folded in two, a portion of the first and second side edge portions of the continuous sheet is cut in a die-cutting process, with the first and second side edge portions lying on top of each other. It is technically difficult to cut a single sheet in a die-cutting process, but cutting a two-folded continuous sheet in a die-cutting process is easier.

In a preferred embodiment of the present invention, the inner surface of the external sheet has a surface with which a male touch fastener can engage; and the method further includes the step of placing the male touch fastener capable of engaging with the engageable inner surface in a detatchable manner, on an outer surface of the absorbent body which faces the inner surface of the external sheet.

With such an embodiment, the absorbent body can be attached to and removed from the external sheet because of the male touch fastener, and it is easy to attach and remove the absorbent body.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

EXAMPLE 1

An embodiment of the present invention will now be described with reference to the drawings.

FIGS. 1A to 3B show Embodiment 1.

Diaper 1:

As shown in FIG. 3A, a diaper (an example of a worn article) 1 includes a crotch portion 10 covering the crotch area of the wearer, a front torso portion 11 covering the front side of the wearer, and a back torso portion 12 covering the back side of the wearer.

The diaper 1 includes an absorbent body 2 and an external sheet 3.

The external sheet 3 is formed by an air-permeable material (e.g., a non-woven fabric).

As shown in FIG. 2B, the absorbent body 2 includes a liquid-absorbing core 22 in between a liquid-permeable top sheet 20 and a liquid-impermeable back sheet 21.

The core 22 is made of pulp, a super absorbing polymer, etc., for example.

A hydrophilic non-woven fabric may be placed on the core 22. The top sheet 20 is made of a non-woven fabric covering the inner surface of the core 22, and a three-dimensional non-woven fabric (cuff) 200 for preventing a side leak may be provided. The back sheet 21 covers the outer surface of the core 22.

As shown in FIG. 3A, the absorbent body 2 is placed on an inner surface 3a of the external sheet 3 and is fastened to be removable.

A front waist portion 13 and a rear waist portion 14, which are not covered by the absorbent body 2, are formed in the front torso portion 11 and the back torso portion 12, respectively, of the external sheet 3.

Figure 3B:
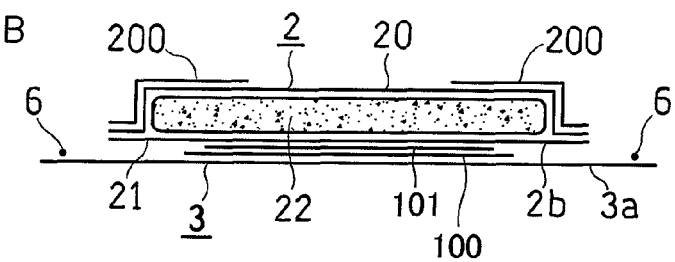
FIG. 3B is a schematic cross-sectional view taken along line IIIB-IIIB of FIG. 3A.

As shown in FIGS. 1A and 3B, a pair of female touch fasteners 100 are bonded to the inner surface 3a of the external sheet 3. The pair of female touch fasteners 100 of FIG. 3A are placed in the front torso portion 11 area and the back torso portion 12 area of the external sheet 3, which are spaced apart from each other in the carrying direction X, and are extending in the girth direction Y.

On the other hand, as shown in FIGS. 1B and 3B, a pair of male touch fasteners 101 are bonded to an outer surface 2b of the absorbent body 2, which faces the inner surface 3a of the external sheet 3. The pair of male touch fasteners 101 of FIG. 3A are placed in end portions of the absorbent body 2, which are spaced apart from each other in the carrying direction X, and are extending in the girth direction Y.

The male touch fasteners 101 engage with the female touch fasteners 100 in a detachable manner. Thus, the absorbent body 2 is attached to the external sheet 3 in a detachable manner.

If the inner surface 3a of the external sheet 3 is formed by a non-woven fabric, it may not be necessary to provide the female touch fasteners 100.

Alternatively, the female touch fasteners 100 may be provided on the absorbent body 2, and the male touch fasteners 101 on the external sheet 3.

An elastic band 4 for expanding and contracting the rear waist portion 14 in the girth direction Y is placed on the rear waist portion 14, which covers the back side of the wearer. The elastic band 4 may be, for example, a plurality of rubber threads or rubber tapes, a material including a film or a thermoplastic resin, or the like.

Therefore, when the diaper 1 is worn, the inner surface 3a of the external sheet 3, made of a non-woven fabric, is in contact with the skin of the wearer in the front waist portion 13. On the other hand, the inner surface 3a of the external sheet 3 is in contact with the skin of the wearer between the elastic band 4 of the rear waist portion 14 and the absorbent body 2.

Fastening members 5 formed by male touch fasteners for example, are provided on opposite end portions of the rear waist portion 14 of the diaper 1 in the girth direction Y. The fastening members 5 may be, for example, tapes with an adhesive applied thereon, instead of the male touch fasteners.

Elastic members 6 made of rubber threads, for example, are placed in the vicinity of opposite side edge portions of the absorbent body 2 in the girth direction Y which correspond to the leg holes Lh of the external sheet 3 so that the external sheet 3 conforms to the legs of the wearer.

Therefore, when wearing the diaper 1, the rear waist portion 14 is fastened to the front waist portion 13 with the fastening members 5 interposed therebetween to squeeze the waist of the wearer, thus securing the diaper 1. As the stretched elastic band 4 contracts, the diaper 1 fits around the waist of the wearer. On the other hand, the elastic members 6 placed in the vicinity of the leg holes Lh shrink, thereby fitting the diaper 1 around the legs of the wearer.

Next, a method for manufacturing the diaper 1 will be described.

Step of Folding Continuous Sheet W1 in Two:

As shown in FIG. 1A, a continuous sheet W1 made of a non-woven fabric is carried in the carrying direction X1. The continuous sheet W1 is a continuous array of the external sheets 3 of FIG. 3 extending in the longitudinal direction X, which is perpendicular to the girth direction Y.

As shown in FIG. 1A, the continuous sheet W1 is folded in two in the girth direction Y while being carried in the carrying direction X1. The continuous sheet W1 is folded in two so that a first side edge portion 31 and a second side edge portion 32 lie on top of each other along the longitudinal direction Y. That is, the continuous sheet W1 is folded in two using the imaginary center line C as the center so that the inner surface 3a of the first side edge portion 31 and the inner surface 3a of the second side edge portion 32 of the continuous sheet W1 come into contact with each other.

Trimming Step:

Then, a portion of the first and second side edge portions 31 and 32 is trimmed off in a die-cutting process, with the first and second side edge portions 31 and 32 lying on top of each other, so that a portion of the first and second side edge portions 31 and 32 is narrowed, thus forming the leg holes Lh.

After the trimming, the first and second side edge portions 31 and 32 are opened apart from each other, after which the elastic bands 4 and the fastening members 5 are placed with predetermined intervals therebetween.

Moreover, the pair of female touch fasteners 100 extending in the girth direction Y are placed in areas of the front torso portion 11 and the back torso portion 12 (FIG. 3A), which are spaced apart from each other in the carrying direction X.

Step of Cutting Off (Severing) Absorbent Body 2:

On the other hand, as shown in FIG. 1B, a continuous laminate W2 is carried in the carrying direction X1. The continuous laminate W2 is a continuous array of the absorbent bodies 2 of FIG. 3 extending in the longitudinal direction X, which is perpendicular to the girth direction Y.

The continuous laminate W2 includes the cores 22 sandwiched between the continuous top sheet 20 and the continuous back sheet 21. As indicated by broken lines in FIG. 1B, the cores 22 are arranged intermittently between the top sheet 20 and the back sheet 21.

The pair of male touch fasteners 101 extending in the girth direction Y are placed in end portions of the absorbent body 2 spaced apart from each other in the carrying direction X.

A tip portion of the continuous laminate W2 in the carrying direction X1 of the continuous laminate W2 is cut off, one after another, along the first cut-off line CL1 which is generally parallel to the girth direction Y to obtain the absorbent bodies 2. As a method for manufacturing the absorbent bodies 2, as shown in FIG. 2A, for example, the continuous laminate W2 is severed one after another by a rotating cutter 40 at a predetermined interval while being carried by a first conveyer 51 to obtain the individual absorbent bodies 2.

Separation Step:

After the severing, as shown in FIG. 1B, the cut-off absorbent bodies 2 are separated from one another in the longitudinal direction X. As a method for separating the absorbent bodies 2 from one another, as shown in FIG. 2A, for example, the absorbent bodies 2 are separated from one another by the re-pitching device 60 after they are handed over from the first conveyer 51 to a re-pitching device 60.

The re-pitching device 60 includes a plurality of pads 61 for receiving the absorbent bodies 2, and the absorbent bodies 2 are separated from one another as the pads 61 rotate apart from one another. The re-pitching device 60, for example, may be a re-pitching drum disclosed in Japanese Laid-Open Patent Publication No. 2006-212307.

Step of Placing Absorbent Body 2:

As shown in FIG. 1C, after the elastic members 6 made of rubber threads, for example, are intermittently placed on the continuous sheet W1 in the longitudinal direction X in the vicinity of the leg holes Lh, the absorbent bodies 2 are intermittently placed on the continuous sheet W1.

In order to place the absorbent bodies 2 on the continuous sheet W1, as shown in FIG. 2A, for example, the absorbent bodies 2 which have been separated from one another by the re-pitching device 60 are placed on the inner surface 3a of the continuous sheet W1 which is being carried on a second conveyer 52.

During the placement, by engaging the pair of male touch fasteners 101, which is bonded to the outer surface 2b of the absorbent body 2, with the female touch fastener 100, which is bonded to the inner surface 3a of the continuous sheet W1 engaging with each other, in a detatchable manner, the absorbent bodies 2 can be attached to the continuous sheet W1 in a detatchable manner.

Step of Obtaining Diaper 1:

Then, as shown in FIG. 1C, the continuous sheet W1 is severed along the second cut-off line CL2, which is generally parallel to the girth direction Y, into individual diapers 1, each including the absorbent body 2 placed on the continuous sheet W1.

EXAMPLE 2

As shown in Embodiment 2 of FIG. 4, the continuous sheet W1 may be formed so that the front torso portions 11 or the back torso portions 12 of adjacent diapers 1 are adjacent to each other.

That is, as shown in FIG. 4A, adjacent back torso portions 12 have the fastening members 5 placed individually thereon, and share a single elastic sheet 4A placed therebetween.

As shown in FIG. 4C, when the adjacent back torso portions 12 are severed from each other along the second cut-off line CL2, the elastic sheet 4A is divided into individual elastic bands 4.

Otherwise, the configurations are similar to that of Embodiment 1, and therefore like elements are denoted by like reference numerals and will not be further described below.

While a preferred embodiment is described above with reference to the drawings, obvious variations and modifications will readily occur to those skilled in the art upon reading the present specification.

For example, two sheets of non-woven fabric may form the external sheet. Alternatively, an elastic member may be placed between two external sheets.

Moreover, the diaper manufactured by the present manufacturing method may be a so-called "pants-type diaper" in which the end portions of the front torso portion and those of the back torso portion are fastened together.

Thus, such variations and modifications shall fall within the scope of the present invention as defined by the appended claims.

INDUSTRIAL APPLICABILITY

The present invention is applicable to methods for manufacturing disposable worn articles.

DESCRIPTION OF THE REFERENCE NUMERALS

1: Diaper (an example of a worn article)
2: Absorbent body
3: External sheet
3a: Inner surface
3C: Severed sheet
4: Elastic band
10: Crotch portion
13: Front waist portion
14: Rear waist portion
20: Top sheet
21: Back sheet
22: Core
31: First side edge portion
32: Second side edge portion
C1: First severed sheet
C2: Second severed sheet
W1: Continuous sheet
W2: Continuous laminate
X: Longitudinal direction
Y: Girth direction

The invention claimed is:

1. A method for manufacturing disposable worn articles, each of the disposable worn articles comprising: an absorbent body including a liquid-permeable top sheet, a liquid-impermeable back sheet and a liquid-absorbing core; and an air-permeable external sheet, wherein the external sheet covers a crotch portion of a wearer with the absorbent body interposed therebetween, and covers a waist of the wearer on a front side and on a back side and configures a waist portion of the worn article where the absorbent body is absent absent, the method comprising the steps of:

carrying a continuous sheet which is the external sheets being continuous in a longitudinal direction perpendicular to a girth direction;

carrying a continuous laminate which is the absorbent bodies being continuous in the longitudinal direction;

cutting off a tip portion of the continuous laminate in a carrying direction to obtain the absorbent bodies one after another;

separating the cut-off absorbent bodies from each other in the longitudinal direction of the absorbent bodies;

placing the absorbent bodies in a detachable manner and intermittently on the continuous sheet so that an inner surface of each of the external sheets is uncovered by each of the absorbent bodies in the waist portion on the front side and on the back side;

severing the continuous sheet between the adjacent absorbent bodies, thereby individually obtaining each of the worn articles having one of the absorbent bodies placed on one of the external sheets;

folding the continuous sheet in two so that a first side edge portion and a second side edge portion along the longitudinal direction of the continuous sheet lie one on top of the other; and trimming a portion of the first and second side edge portions in a die-cutting process, with the first and second side edge portions lying one on top of the other, so that the portion of each of the first and second side edge portions has a narrowed portion.

2. The method for manufacturing disposable worn articles according to claim 1, wherein each of the external sheets includes an elastic band for expanding and contracting a rear waist portion thereof placed on the rear waist portion which covers the back side of the waist of the wearer, and the inner surface of each of the external sheets is exposed between the elastic band and each of the absorbent bodies so as to be in contact with skin of the wearer.

3. The method for manufacturing a disposable worn article according to claim 2 wherein:

the method further comprises the step of placing a male touch fastener on an outer surface of the absorbent body which faces an inner surface of the continuous sheet;

the inner surface of the continuous sheet has a surface with which the male touch fastener is engageable; and the male touch fastener is capable of engaging with the engageable inner surface in a detachable manner.

4. The method for manufacturing a disposable worn article according to claim 2 wherein:

the method further comprises the steps of: opening the first and second side edge portions apart from each other after the step of trimming; and after the step of opening, placing the elastic bands with predetermined intervals therebetween.

5. The method for manufacturing a disposable worn article according to claim 1 wherein:

the method further comprises the step of placing a male touch fastener on an outer surface of the absorbent body which faces an inner surface of the continuous sheet;

the inner surface of the continuous sheet has a surface with which the male touch fastener is engageable; and the male touch fastener is capable of engaging with the engageable inner surface in a detachable manner.

\* \* \* \* \*